United States Patent [19]
Ota

[11] Patent Number: 6,110,165
[45] Date of Patent: Aug. 29, 2000

[54] APPARATUS FOR LASER TREATMENT

[75] Inventor: Yasuo Ota, Gamagori, Japan

[73] Assignee: Nidek Co., Ltd., Japan

[21] Appl. No.: 08/609,931

[22] Filed: Feb. 28, 1996

[30] Foreign Application Priority Data

Feb. 28, 1995 [JP] Japan .................................. 7-68637
Mar. 31, 1995 [JP] Japan .................................. 7-99662

[51] Int. Cl.[7] .............................................. A61B 18/18
[52] U.S. Cl. ................................ 606/4; 606/3; 606/11; 606/12
[58] Field of Search ..................... 606/4, 5, 6, 10, 606/11, 12, 3, 15, 16, 17, 18

[56] References Cited

U.S. PATENT DOCUMENTS

| | | | |
|---|---|---|---|
| 4,486,440 | 12/1984 | Emanuel et al. | 424/263 |
| 4,520,816 | 6/1985 | Schachar et al. | 606/4 |
| 4,573,465 | 3/1986 | Sugiyama et al. | 128/303.1 |
| 4,750,829 | 6/1988 | Wise | 351/160 R |
| 4,917,486 | 4/1990 | Raven et al. | 351/221 |
| 5,139,494 | 8/1992 | Freiberg | 606/10 |
| 5,147,349 | 9/1992 | Johnson et al. | 606/15 |
| 5,188,633 | 2/1993 | Kratzer et al. | 606/12 |
| 5,300,062 | 4/1994 | Ueno | 606/4 |
| 5,312,396 | 5/1994 | Feld et al. | 606/11 |
| 5,348,551 | 9/1994 | Spears et al. | 606/10 |
| 5,403,306 | 4/1995 | Edwards et al. | 606/2 |
| 5,662,644 | 9/1997 | Swor | 606/10 |
| 5,776,127 | 6/1998 | Anderson et al. | 606/15 |
| 5,782,822 | 7/1998 | Telfair et al. | 606/3 |
| 5,836,909 | 11/1998 | Cosmescu | 606/15 |

Primary Examiner—Linda C. M. Dvorak
Assistant Examiner—Sonya Harris-Ogugua
Attorney, Agent, or Firm—Rossi & Associates

[57] ABSTRACT

To achieve highly efficient laser irradiation and well-balanced light coagulation treatment within a same treatable site by using laser beam of different wavelengths, an apparatus is disclosed which comprises a plurality of laser light sources for treatment which emit laser beams of different wavelengths, a condition setting device for determining irradiation condition of the laser light sources, a control device for controlling the laser light sources according to the settings determined at the condition setting device so as to sequentially irradiate laser beams, and a guide device for directing emitted laser beams into an eye of a patient.

10 Claims, 3 Drawing Sheets

APPARATUS FOR LASER TREATMENT

BACKGROUND OF THE INVENTION

1. Field of the Invention

The present invention relates to an apparatus for laser treatment by irradiating therapeutic laser beam to an eye of a patient.

2. Description of the Related Art

An apparatus for laser therapy for coagulation by irradiating therapeutic laser beam to an eye of a patient is well-known so far. A variety of wavelengths of therapeutic beam from the laser therapy apparatus are used, ranging from visible light to infrared. The selection of the wavelength of therapeutic laser beam is made by taking account for the absorption characteristics of the area to be cured.

When, for example, an attempt is made to treat a retinal separation at an ocular fundus by coagulation through such layers as intraretinal, retinal pigment epithelium (called as "pigment epithelium" in the specification below), and choroid, one wavelength results in selective coagulation of one layer. This means that a shorter wavelength may strongly coagulate the intraretinal layer, whereas a longer wavelength may coagulate primarily the choroid layer. In order to obtain a coagulation from an intra-layer to a fundus layer, laser beams of different wavelengths must be irradiated. As the different wavelengths are irradiated by separate operation, laser irradiation to the identical site to be treated may be so difficult that the efficiency will be poor. Further, if laser beam of a longer wavelength is irradiated after a shorter wavelength, a degenerated and coagulated layer prevents laser beam from penetrating into deeper layers.

SUMMARY OF THE INVENTION

The present invention has been made in view of the above circumstances and is intended to overcome the above problems. It is an object of the present invention to provide an apparatus for laser therapy which may treat sufficiently the same site to be treated by using laser beams of different wavelengths to enable more efficient laser irradiation to be achieved.

Additional objects and advantages of the present invention will be set forth in part in the description which follows and in part will be obvious from the description, or may be learned by practice of the present invention. The objects and advantages of the invention may be realized and attained by means of the instrumentalities and combinations particularly pointed out in the appended claims.

To achieve the objects and in accordance with the purpose of the present invention, as embodies and broadly described herein, an apparatus for laser treatment of this invention comprises a plurality of laser light sources for treatment for emitting laser beams of different wavelengths, a means for setting irradiation condition for each of the laser beam emitted from each of the laser light sources, a control means for controlling sequential emission of each laser beam from each of the laser light sources in accordance with the irradiation condition predetermined by the means for setting irradiation condition of the laser beam from each of the laser light sources, and a guide means for guiding the laser beam emitted from the laser light source into an eye of a patient in accordance with the control by the control means.

The control means is such that laser beam of a longer wavelength among laser beams of different wavelengths is irradiated at first.

The means for setting irradiation condition comprises a setting means for determining the duration and the power of irradiation of the each of laser light beams.

The laser beams of different wavelengths emitted from the plurality of laser light sources comprise lasers of a wavelength longer than about 600 nm and that shorter than about 600 nm.

The laser beam of the wavelength longer than about 600 nm comprises Krypton laser, and the laser beam of the wavelength shorter than about 600 nm comprises Argon laser.

Another apparatus for laser treatment of this invention comprises a single laser light source for emitting laser beams of different wavelengths, a guide means for directing the light beam emitted from the laser light source into an eye of a patient, a means for setting irradiation condition for laser beam to be irradiated to an eye of a patient, a means for selecting the wavelength of the laser beam emitted from the laser beam light source, and a control means for controlling the wavelength selecting means for driving the laser light source so as to sequentially emit the laser beams of different wavelengths in accordance with the irradiation condition of the laser beams predetermined by the means for setting irradiation condition.

The wavelength selecting means comprises a plurality of filters having transmittance characteristics corresponding to the wavelength of the laser beam emitted from the laser beam light source, and a means for selecting and interchanging one of the plurality of filters to place it into light path.

The laser beam emitted from the laser beam light source comprises Krypton laser beam having a plurality of dominant wavelengths.

According to the present invention, highly efficient and well-balanced light coagulation for the different layers within a same site to be treated may be achieved with only one operation of laser irradiation.

BRIEF DESCRIPTION OF THE DRAWINGS

Other features and advantages of the invention will be apparent from the following description taken on connection with the accompanying drawings, in which.

DETAILED DESCRIPTION OF THE PREFERRED EMBODIMENTS (First Embodiment)

Figure 1:
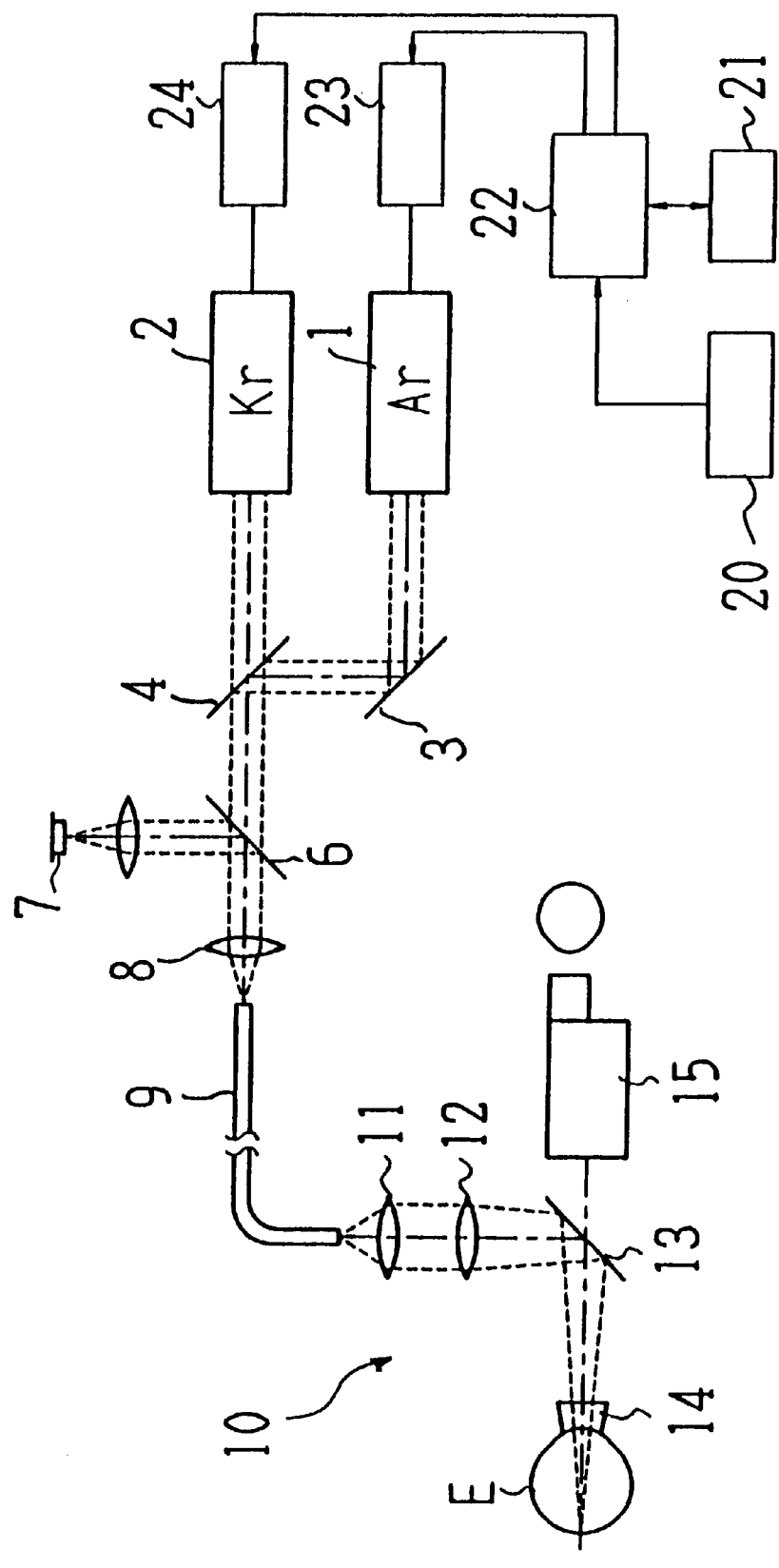
FIG. 1 shows the architecture of an apparatus of a first embodiment according to the present invention.

The present invention will be described by way of preferred embodiments thereof with reference to the accompanying drawings. Now referring to FIG. 1, which schematically depicts the architecture of an apparatus of the present invention.

(Optics)

Reference numeral 1 designates a light source of Argon laser beam for emitting laser beam of dominant wavelength of 514.5 nm, 2 is a light source of Krypton laser beam for emitting laser beam of dominant wavelength of 647.1 nm. 3 is a reflector for directing the light path of the Argon laser beam emitted from the light source 1. 4 is a dichroic mirror for registering the light axis of the laser beam emitted from the Krypton light source 2 with the light axis of the Argon laser beam reflected by the reflector 3. As will be described in detail hereinafter, a detachable mirror may be provided which is inserted and removed in synchronism to the emission of respective laser beams, instead of the dichroic mirror 4, since each laser beam is emitted separately.

Reference numeral 6 designates a dichroic mirror. Emitting light bundle of visible light semiconductor laser 7 for aiming (dominant wavelength: 635 nm.) is corrected to be circular to register with treatment laser beam. 8 is a focusing lens which captures laser beam to output into an optical fiber 9.

The optical fiber 9 directs the laser beam to an irradiation station 10. The laser beam passed through the optical fiber 9 is directed through a collimator lens 11, a focusing leans 12, a mirror 13, and a contact lens 14 to the eye of a patient (E). Reference numeral 15 designates a binocular microscope for observing the patient's eye E by the eyes of an operator.

(Control System)

Reference numeral 20 is an irradiation switch for transmitting a trigger signal of the laser irradiation. 21 is an operation console comprising mode switches for input of conditions of laser coagulation and for selection of treatment laser beam to be emitted. The irradiation switch 20 and the operation console 21 are connected to a control station 22. The control station 22 receives a signal from the irradiation switch 20 as well as a signal of setting condition from the operation console 21, to control laser emission from respective laser light sources by transmitting the signals to a power supply 23 for the Argon laser light source 1 and a power supply 24 for the Krypton laser light source 2.

The operation of the apparatus of above mentioned architecture will be now described below.

The operator may select a laser to be used according to the case and/or the site to be treated. The sequential irradiation of laser beams of different wavelengths, by which the present invention is characterized, will be described in detail.

The operator selects a continuous irradiation mode of the Krypton and Argon lasers from the operation console 21, then determines the irradiation condition required for that mode, such as the duration and the power of each laser beam irradiation. When the apparatus is ready, the operator determines the site to be treated by aid of aiming light from the visible semiconductor laser 7 while observing the patient's eye through the microscope 15, and thereafter pushes the irradiation switch 20 to start coagulation.

Figure 2:
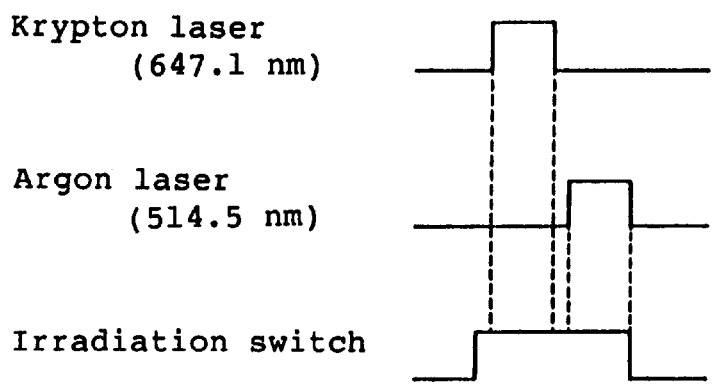
FIG. 2 shows an example of the state of the output of each laser at the time a trigger signal is transmitted.

FIG. 2 shows an example of the state of the output of each laser at the time a trigger signal is transmitted from the irradiation switch 20. Upon reception of a trigger signal, the control station 22 controls the Krypton laser light source 2 through its power supply 24 to cause irradiation of the laser beam of a long wavelength according to the predetermined irradiation condition. Then it controls the Argon laser light source 1 through its power supply 23 to cause irradiation of the laser beam of a short wavelength for the predetermined duration of time.

Figure 3:
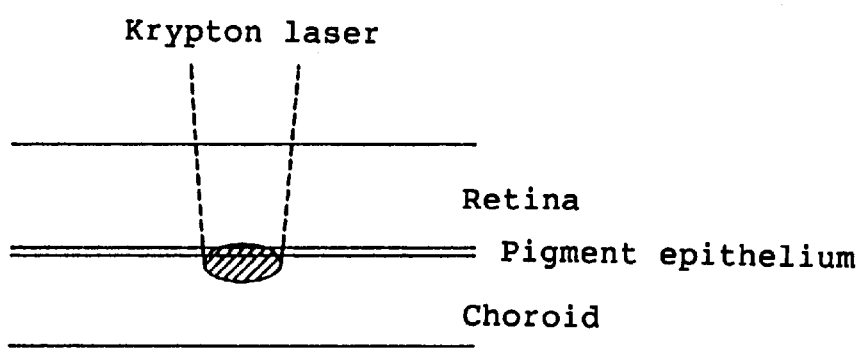
FIGS. 3(a) and 3(b) show coagulation by irradiation of Krypton laser and Argon laser.
Figure 3:
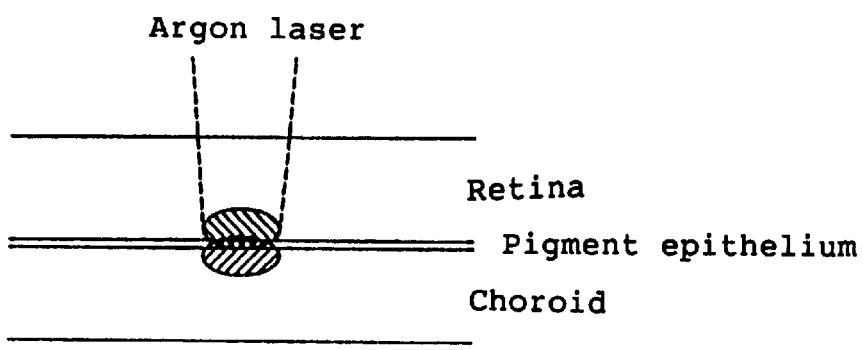

Each of the laser beams emitted by respective light sources is irradiated through the irradiation station 10 to the ocular fundus of the patient's eye (E) in sequence with a certain time delay. The Krypton laser irradiation coagulates the pigment epithelium layer and the choroid layer in accordance with the characteristics of that wavelength as shown in FIG. 3(*a*). The next Argon laser irradiation coagulates the retina and the pigment epithelium layer as shown in FIG. 3(*b*).

As can be appreciated from the above description, efficient coagulation can be obtained for different layers within a same site, with a single operation by irradiating a laser of a long wavelength at first, then a laser of a short wavelength. For the treatment of the retinal detachment in particular, well-balanced coagulation can be obtained in both the retinal side and the choroid side, resulting in efficient adhesion. In addition, the duration and the power of irradiation of each laser may be varied through the operation console 21 for the coagulation site or the case.

In the preferred embodiment mentioned above, the Krypton laser is used as a laser of a long wavelength and the Argon laser is used as a laser of short wavelength. Combination of other lasers of different wavelengths may be conceivable. Especially for the light coagulation treatment of ocular fundus, a combination of a laser of a wavelength longer than about 600 nm with another one shorter than that is preferred. The reason is that in case of light coagulation treatment, most irradiated laser beam will be absorbed by pigment epithelium and choroid, that the melanin pigment contained in the choroid exhibits high optical density in wavelengths ranging from ultraviolet to almost all visible light, and that in particular increased permeability and decreased absorbance will be observed for longer wavelengths than about 600 nm. For example, second harmonics of an Nd:YAG laser (dominant wavelength: 532 nm) may be usable for a laser not longer than 600 nm, and a semiconductor laser of 670 nm or an Nd:YAG laser of 1,064 nm, for a laser longer than 600 nm.

Also, a combination with a variety of lasers having a variety of characteristics such as the dye laser of variable wavelength (dominant wavelength: 574 to 640 nm) may be possible. Combination of more than two lasers may be used as well.

(Second Embodiment)

In the first embodiment two different laser beam light sources of the Krypton and Argon lasers are used for light sources emitting therapeutic laser beam of different wavelengths. In the second embodiment, only one laser light source which may emit laser beam of different wavelengths will be used for selecting wavelengths of the laser beam emitted therefrom.

Figure 4:
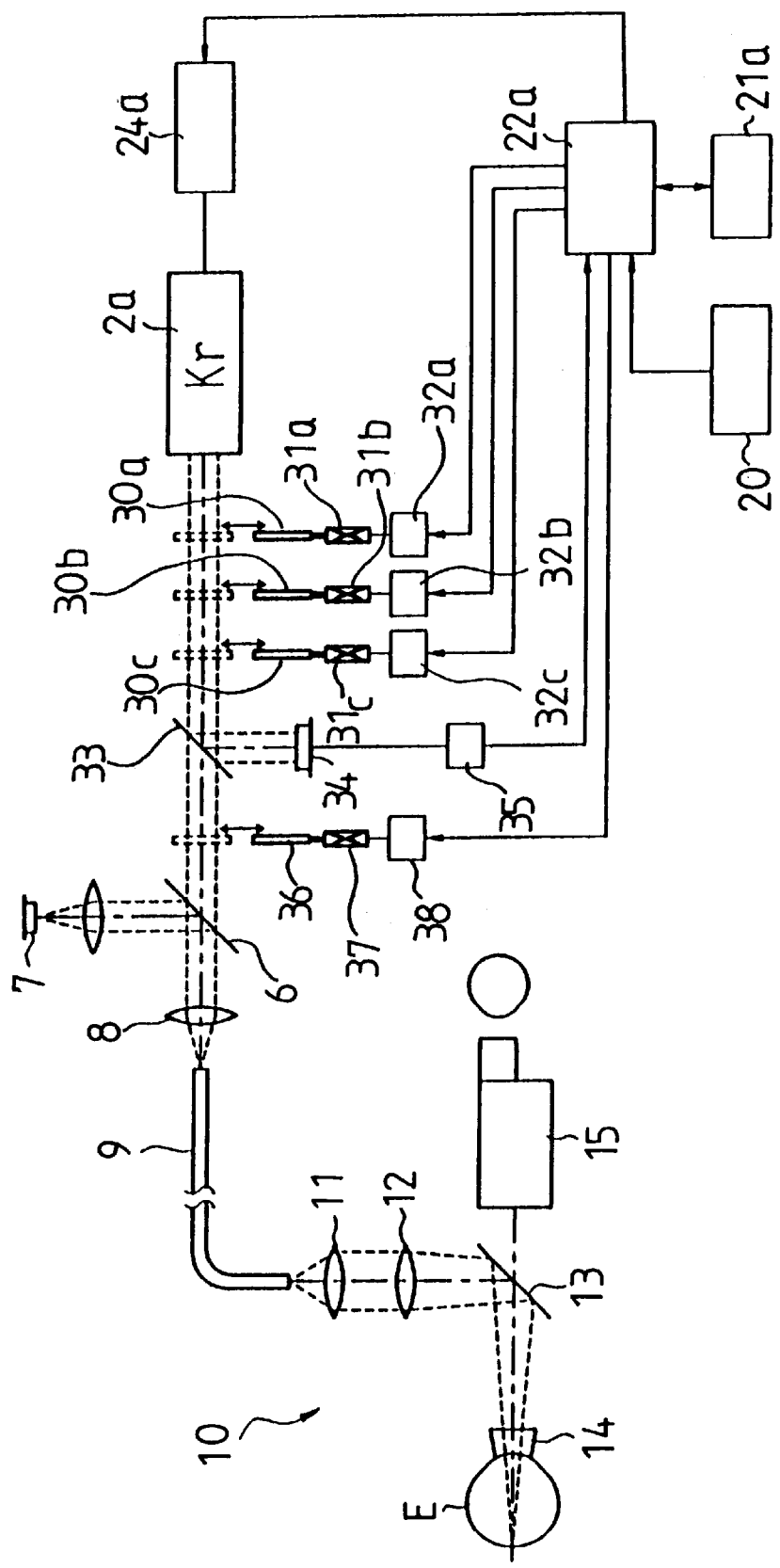
FIG. 4 shows the architecture of an apparatus of a second embodiment according to the present invention.

FIG. 4 shows a schematic diagram of an apparatus of the second embodiment according to the present invention. Like numerals refer to like parts, the description of which will be omitted.

Reference numeral 2*a* designates a Krypton laser light source, which emits green lasers of dominant wavelengths 520.8 nm and 530.9 nm, an yellow laser of wavelength 568.2 nm, and a red laser of wavelength 647.1 nm.

Reference numerals 30*a*, 30*b* and 30*c* refer to filters for selecting one of the wavelengths from laser beam emitted from the Krypton laser light source 2*a*. Each of the filters 30*a*, 30*b* and 30*c* has selective transmittance of the green laser beams, yellow beam and red beam, respectively. Reference numerals 31*a*, 31*b* and 31*c* are solenoids for inserting/removing respective filters 30*a*, 30*b*, 30*c*, and 32*a*, 32*b* and 32*c* are drivers for driving respective solenoids. Alternatively, a wavelength selecting system comprised of these filters 30*a*–30*c*, solenoids 31*a*–31*c*, and drivers 32*a*–32*c* may be such that each filter is held on a turret which in turn is driven so as to insert/remove one of the filters into/from the light path.

Reference numeral 33 designates a beam splitter, 34 a light detector. Laser beam is emitted from the Krypton laser light source 2*a*. Part of the laser beam is filtered by the filters 30a–30c, reflected by the beam splitter 33, and finally received by the detector 34. The detector 34 monitors the output of the laser beam based on the amount of the light received. A signal from the detector 34 is processed at a detection processing circuit 35 to be transmitted to the control station 22a. The control station 22a sends an output adjusting signal to the power supply 24a, based on the laser output signal processed by the detection processing circuit 35 and the output signal predetermined at the operation console 21a, so as to coincide and stabilize the output of laser beam with the preset value.

Reference numeral 36 is a safety shutter which is driven by solenoid 37, to be inserted into the light path in a predetermined event in order to shut the beam off. 38 is a driver for the solenoid 37.

In the operation of the apparatus of the second embodiment, continuous irradiation of different wavelengths, similar to that of the first embodiment above, will be described below.

The operator selects the laser wavelength to be sequentially irradiated at the operation console 21a, and determines the condition such as the duration and the power of irradiation. Now assume that red and green lasers have been selected as lasers to be used. The control station 22a receives a wavelength selection signal, then drives the solenoid 31c to insert the filter 30c for transmitting red laser beam. On the other hand, the safety shutter 35 is initially placed on the light path to block beam. When the irradiation switch 20 is pushed down, the control station 22a receives a trigger signal, and drives the power supply 24a to operate the Krypton laser beam light source 2a to irradiate laser beam. The laser beam emitted from the Krypton laser light source 2a is filtered by the filter 30c to transmit selectively red laser beam of a long wavelength. Part of laser beam passing through the filter 30c is detected by the detector 34. The control station 22a verifies the laser output power based on the detection signal to appropriately supply power to the power supply 24a to drive the Krypton laser light source 2a so as to irradiate laser beam with predetermined power level, then the safety shutter 35 will be opened. Laser beam passing through the safety shutter 35 is transmitted through the focusing lens 8, optical fiber 9, irradiation station 10 to the patient's eye. Due to the characteristics of wavelength, the red laser beam will coagulate the pigment epithelium layer and choroid layer of the ocular fundus of the patient.

When a predetermined duration of irradiation of the red laser beam is reached, the control station 22a closes the safety shutter 35 and replaces filter 30c with the filter 30a. As the replaced filter selectively transmits 'green' laser beam of a short wavelength. Laser beam passing through the filter 30a is detected by the detector 34. After stabilizing the laser power to a predetermined level, the control station 22a opens the safety shutter 35 for a predefined period of time. While the safety shutter 35 opens, a short wavelength laser (green laser) is irradiated to the ocular fundus of the patient for the coagulation of the retina and the pigment epithelium, subsequent to the previous coagulation.

Although there has been described the case in which red beam (dominant wavelength: 647.1 nm) and green beams (520.8 nm and 530.9 nm) were selected, a combination of red beam and yellow beam (568.2 nm) may be used instead, or red, yellow, green lasers may be sequentially irradiated, according to the case or the site to be treated. In addition, both yellow and green lasers may be irradiated simultaneously after irradiation of red laser beam. In the latter case, another filter for transmitting both yellow and green laser beams should be added to the optics, which are controlled by the control station 22a for insertion/removal.

As can be appreciated, in this second preferred embodiment, by selecting at first a longer wavelength laser then a shorter wavelength laser among different beams emitted from one single laser light source, coagulation of higher efficiency for different layers within a same site may be achieved, similar to the first embodiment described above.

In the second preferred embodiment, Krypton laser is used as the source for beams of some different wavelengths, a dye laser may be used instead, which may emit laser beams of wavelength range from 574 to 640 nm. When using a dye laser for the light coagulation treatment, a combination of filters for wavelength range not longer than 600 nm and longer than 600 nm may be provided to select the range.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the present invention and its practical application to enable one skilled in the art to utilize the present invention in various embodiments and with various modifications as are suited to the particular use contemplated. It is intended that the scope of the present invention be defined by the claims appended hereto, and their equivalents.

What is claimed is:

1. An apparatus for laser treatment, comprising:
   a plurality of laser light sources for emitting a plurality of laser beams of different wavelengths for coagulation treatment of a treatment area;
   means for setting an irradiation condition for each laser beam emitted from each of said laser light sources;
   control means for controlling sequential emission of each laser beam from each of said laser light sources in response to a trigger signal in accordance with the irradiation condition set by said means for setting, wherein a long wavelength laser beam of said plurality of laser beams is emitted before a short wavelength laser beam of said plurality of laser beams; and
   guide means for guiding each laser beam emitted from each said laser light source into the treatment area of an eye of a patient in accordance with the control by said control means, wherein the treatment area is the fundus of the eye.

2. An apparatus according to claim 1, wherein said means for setting irradiation condition comprises setting means for determining the duration and the power of irradiation of said each of laser light beams.

3. An apparatus according to claim 1, wherein said long wavelength laser beam has a wavelength longer than 600 nm and said short wavelength laser beam has a wavelength that is shorter than 600 nm.

4. An apparatus according to claim 3, wherein the long wavelength laser beam comprises a Krypton laser beam, and wherein the short wavelength laser beam comprises an Argon laser beam.

5. An apparatus for laser treatment, comprising:
   Krypton laser light source for emitting Krypton laser beam for coagulating the pigment epithelium layer and the choroid of an eye of a patient;
   Argon laser light source for emitting Argon laser beam for coagulating the retina and the pigment epithelium layer of an eye of a patient;

guide optics for guiding Krypton laser beam emitted from said Krypton laser light source and Argon laser beam emitted from said Argon laser light source into the eye of the patient;

means for setting irradiation condition for said Krypton laser beam and said Argon laser beam; and control means for controlling sequential emission of said Krypton laser beam and said Argon laser beam in response to a trigger signal in accordance with the irradiation condition determined by said means for setting irradiation condition.

6. An apparatus according to claim 5, wherein said control means comprises means for driving the Krypton laser light source then the Argon laser light source to treat an identical area of an eye of a patient.

7. An apparatus according to claim 5, wherein said means for setting irradiation condition comprises means for determining the duration and the power of respective irradiations of the Krypton laser beam and the Argon laser beam emitted from respective Krypton laser light source and the Argon laser light source.

8. An apparatus according to claim 5, wherein said guide optics comprises:

optical means for combining the Argon laser beam emitted from said Argon laser light source into the optics for the Krypton laser beam emitted from said Krypton laser light source; and optical element for reflecting said Argon laser beam into said point in the optics at which said laser beam is combined by said optical means to guide it to the patient's eye, and for passing said Krypton laser beam through the optics to guide it thereto.

9. An apparatus for laser treatment, comprising:

a light source for emitting a light beam having a plurality of peak wavelengths proper for coagulation treatment of the fundus;

guide means for directing the light beam emitted from said laser light source along a light path and into an eye of a patient;

means for setting an irradiation condition for a light beam to be irradiated to an eye of a patient;

means for selecting one of the peak wavelengths of the light beam emitted from said laser beam light source as a selected wavelength of the light beam to be irradiated to the eye of the patient, wherein said means for selecting comprises a plurality of filters having a plurality of transmittance characteristics, and an automated insertion/removal device for selectively placing one of said plurality of filters into the light path prior to the eye of the patient to produce the selected wavelength; and control means for controlling said wavelength selecting means and for driving said laser light-source, so as to sequentially emit light beams of different wavelengths in accordance with the irradiation condition set by said means for setting to cause coagulation of the fundus.

10. An apparatus according to claim 9, wherein the light beam emitted from said light source comprises a Krypton laser beam having a plurality of dominant wavelengths.

* * * * *